United States Patent
Brugger et al.

(10) Patent No.: US 6,558,374 B1
(45) Date of Patent: May 6, 2003

(54) LASER-OPERATED DENTAL HANDPIECE

(75) Inventors: Wilhelm Brugger, Bergheim bei Salzburg (AT); Johann Haberl, Nussdorf am Haunsberg (AT)

(73) Assignee: Dentalwerk Bürmoos Gesellschaft m.b.H., Bürmoos (AT)

( * ) Notice: Subject to any disclaimer, the term of this patent is extended or adjusted under 35 U.S.C. 154(b) by 0 days.

(21) Appl. No.: 08/477,878

(22) Filed: Jun. 7, 1995

(30) Foreign Application Priority Data

Jun. 13, 1994 (AT) ............................................. 1173/94

(51) Int. Cl.⁷ .............................................. A61G 18/22
(52) U.S. Cl. ............................. 606/15; 606/13; 606/17; 433/29
(58) Field of Search ..................... 606/2, 3–18; 433/24, 433/215

(56) References Cited

U.S. PATENT DOCUMENTS 5,346,489 A * 9/1994 Levy et al. .................... 606/15

* cited by examiner

*Primary Examiner*—David M. Shay
(74) *Attorney, Agent, or Firm*—Friedrich Kueffner

(57) ABSTRACT

A dental or surgical handpiece which operates on the basis of laser includes a light guide for the laser which, in order to ensure the relative rotation between supply hose and handpiece, is arranged concentrically in the coupling between the supply hose and the handpiece. The light guide of the supply hose extends in one piece into the handpiece and, starting from the coupling with the supply hose, the light guide is displaced increasingly eccentrically toward the inner side of the bend of the angle piece, and the end of the light guide is rotatably mounted in a receiving unit of the handpiece.

2 Claims, 1 Drawing Sheet

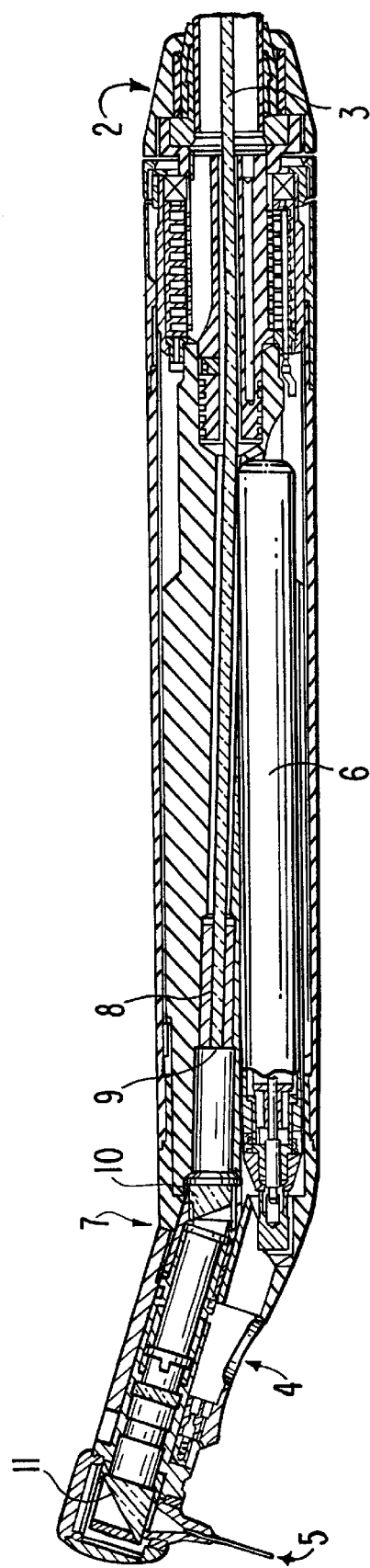

LASER-OPERATED DENTAL HANDPIECE

BACKGROUND OF THE INVENTION

1. Field of the Invention

The present invention relates to a dental or surgical handpiece which operates on the basis of laser and in which, in order to ensure the relative rotation between supply hose and handpiece, the light guide for the laser is arranged concentrically in the coupling between the supply hose and the handpiece.

2. Description of the Related Art

Laser handpieces of the above-described type are increasingly used in the past years in small surgery and microsurgery, but also in dental medicine.

Particularly in the field of dental medicine, in contrast to, for example, brain surgery, various special conditions of the laser exist which prevent the use of laser tools, for example, from brain surgery without substantial modification in dental medicine.

For example, it is particularly necessary in dental treatment to use angle pieces in order to reach locations in the mouth of the patient which would otherwise be difficult to reach. Such angle pieces have long been used and are generally known in conventional mechanical dental handpieces. A significant requirement of such handpieces is the fact that they must be arranged freely rotatable relative to the supply hose.

When producing handpieces operating on the basis of laser, there is the difficulty that it is absolutely necessary to conduct the operating noise of the laser as a controlled variable to the supply unit, wherein a first processing of the signals obtained by small microphones still in the handpiece is a necessity. In spite of all miniaturization, the corresponding electronic equipment requires a volume which is not readily available in the handpiece because the light guide for the laser must be conducted from the supply hose to the handpiece head.

SUMMARY OF THE INVENTION

Therefore, it is the primary object of the present invention to provide a dental handpiece which operates on the basis of laser, in which the problems described above are avoided.

In accordance with the present invention, the light guide of the supply hose extends in one piece into the handpiece and, starting from the coupling with the supply hose, the light guide is displaced increasingly eccentrically toward the inner side of the bend of the angle piece, and the end of the light guide is rotatably mounted in a receiving means of the handpiece.

The configuration of the present invention makes it possible that a light guide coupling in the area of the hose connection becomes unnecessary, so that the intensity of the laser is conducted in the best possible manner to the exit location. In addition, it is made possible to provide sufficient space for the electronic equipment on the underside of the laser handpiece, so that especially the diameter of the handpiece according to the present invention is reduced as compared to those of the state of the art. Another unexpected advantage is the fact that the laser beam only has to be refracted in the area of the bend of the handpiece with a smaller angle than the angle of the handpiece; this is an advantage for the optical equipment which conducts the laser beam away from the end of the light guide.

The various features of novelty which characterize the invention are pointed out with particularity in the claims annexed to and forming a part of the disclosure. For a better understanding of the invention, its operating advantages, specific objects attained by its use, reference should be had to the drawing and descriptive manner in which there are illustrated and described preferred embodiments of the invention.

BRIEF DESCRIPTION OF THE DRAWING

In the drawing:

The single FIGURE of the drawing is a longitudinal sectional view of the dental handpiece according to the present invention.

DESCRIPTION OF THE PREFERRED EMBODIMENTS

As illustrated in the drawing, a dental laser handpiece is rotatably connected to a supply hose 2 by means of a rotating coupling. As known from mechanical dental handpieces, air and pressurized water for forming a spray for cooling the work location is supplied to the laser handpiece. Also supplied to the laser handpiece is the actual work energy, in the present case the laser light supplied through a light guide 3.

Contrary to mechanical handpieces, a number of information data are supplied from the handpiece through the supply hose to the supply unit, so that the operation of the laser can be adapted to the existing situation.

Of particular interest and importance in the handpiece according to the present invention is the pickup of the operating noises of the laser through an opening 4 in the area of the light exit 5 at the tip of the handpiece head.

The operating noises are picked up by means of miniaturized microphones and are subjected to a first processing in an electronic unit 6.

In order to provide space for this evaluating unit 6, the present invention provides that the light guide 3, which is fixedly arranged in the supply hose, extends concentrically through the area of the handpiece coupling and further to near the bend 7 of the laser handpiece 1.

In the handpiece 1, the light guide 3 extends increasingly from the center of the handpiece cross-section toward the inner side of the bend 7 and finally into a receiving means 8 which is rotatable and axially immovably coupled to the handpiece. The light guide 3 is fixedly connected to the receiving means 8, so that, in the case of a relative rotation between the handpiece 1 and the supply hose 2, the light guide 3 does not rotate together with the handpiece 1, but that only the bending plane of the light guide 3 rotates.

At the end 9 of the light guide 3 at the side of the handpiece head, the laser beam is conducted onto an optical unit 10 in which the laser beam is deflected in such a way that it is conducted to the head mirror 11. Since the light guide 3 is not only displaced from the center of the handpiece 1, but also extends inclined relative to the axis of the long portion of the handpiece 1, the optical unit 10 must refract the laser beam by a significantly smaller angle than the angle of the bend of the handpiece 1. For this reason, the errors which unavoidably occur in any real optics, are smaller and the focusing of the laser beam and, thus, its intensity, is improved.

The present invention is not limited to the illustrated embodiment. Thus, in handpieces in which the bending angle at the bend 7 is relatively small and in which the head is not replaceable, it may be possible that the light guide 3 extends close to the area of the head mirror 11 and, thus, to omit the optical unit 10. On the other hand, it may be an advantage if the light guide 3 extends into the handpiece 1 by a smaller distance than in the illustrated embodiment, if this is made possible or useful by the configuration of the electronic equipment 6.

The invention is not limited by the embodiments described above which are presented as examples only but can be modified in various ways within the scope of protection defined by the appended patent claims.

We claim:

1. A laser-operated dental or surgical handpiece, the handpiece comprising a long portion and a short portion extending at an angle relative to each other and forming a bend therebetween, the bend having an inner side, a coupling for connecting a supply hose to the handpiece, a light guide for the laser extending concentrically through the coupling to ensure a relative rotation between the handpiece and the supply hose, the light guide extending from the supply hose into the handpiece, the light guide extending increasingly eccentrically from the coupling toward the inner side of the bend, the light guide having an end within the handpiece, a receiving means being mounted in the handpiece, the end of the light guide being rotatably mounted in the receiving means.

2. The handpiece according to claim 1, wherein the long portion of the handpiece has an axis, and wherein the end of the light guide in the handpiece extends obliquely relative to the axis of the long portion of the handpiece.

* * * * *